US012723016B2

(12) United States Patent
Wang

(10) Patent No.: US 12,723,016 B2
(45) Date of Patent: Sep. 1, 2026

(54) SPLEEN-TARGETED IONIZABLE LIPID COMPOUND, COMPOSITION COMPRISING SAME AND USE THEREOF

(71) Applicant: BEIJING CARRIUS BIO LTD., Beijing (CN)

(72) Inventor: Ming Wang, Beijing (CN)

(73) Assignee: Beijing Carrius Bio Ltd., Beijing (CN)

( * ) Notice: Subject to any disclaimer, the term of this patent is extended or adjusted under 35 U.S.C. 154(b) by 0 days.

(21) Appl. No.: 19/177,328

(22) Filed: Apr. 11, 2025

(65) Prior Publication Data

US 2025/0236585 A1 Jul. 24, 2025

Related U.S. Application Data

(63) Continuation of application No. PCT/CN2024/143257, filed on Dec. 27, 2024.

(30) Foreign Application Priority Data

Dec. 29, 2023 (CN) ......................... 202311865464.4

(51) Int. Cl.

| | |
|---|---|
| ***C07C 211/01*** | (2006.01) |
| ***A61K 39/385*** | (2006.01) |
| ***C07C 9/22*** | (2006.01) |
| ***C07C 43/03*** | (2006.01) |
| ***C07C 59/305*** | (2006.01) |
| ***C07C 219/06*** | (2006.01) |
| ***C07C 323/12*** | (2006.01) |
| *A61K 39/00* | (2006.01) |

(52) U.S. Cl.
CPC .......... *C07C 211/01* (2013.01); *A61K 39/385* (2013.01); *C07C 9/22* (2013.01); *C07C 43/03* (2013.01); *C07C 59/305* (2013.01); *C07C 219/06* (2013.01); *C07C 323/12* (2013.01); *A61K 2039/53* (2013.01)

(58) Field of Classification Search
USPC .......................................................... 568/75
See application file for complete search history.

(56) References Cited

FOREIGN PATENT DOCUMENTS

| | | | |
|---|---|---|---|
| CN | 110101665 | * | 8/2019 |
| CN | 116730857 | A | 9/2023 |
| WO | 2023165595 | A1 | 9/2023 |

OTHER PUBLICATIONS

Qiu et alPNAS 2022 vol. 119 No. 8, 1-10.*
Chang et al., “Enzyme—Instructed Activation of Pro-protein Therapeutics (PPT) In Vivo”, Journal of the American Chemical Society, Oct. 7, 2019, vol. 141, Issue 45, 16 pages.
English, Russell, International Search Report and Written Opinion, International Searching Authority, European Patent Office, PCT/CN2024/143257, May 7, 2025.
Liang et al., “Selective RNA Interference and Gene Silencing Using Reactive Oxygen Species-responsive Lipid Nanoparticles”, Chemical Communications, Jun. 13, 2019, 55, pp. 8170-8173.
Liu et al., “Reactive Oxygen Species—Responsive Lipid Nanoparticles for Effective RNAi and Corneal Neovascularization Therapy”, ACS Appl. Mater. Interfaces, Apr. 5, 2022, 14, 17022-17031.
Office Action and Search Report, Application No. 202311261516.7, China National Intellectual Property Administration, Jun. 5, 2024.
Wang et al., “Spleen-targeted nanosystems for immunomodulation”, Nano Today, Oct. 2023, 52, 101943, 20 pages.

* cited by examiner

*Primary Examiner* — Ana Z Muresan
(74) *Attorney, Agent, or Firm* — Travis Young; Bozicevic, Field & Francis LLP

(57) ABSTRACT

The present invention provides an ionizable lipid compound, which can target spleen for delivery of biological macromolecules including nucleic acid drugs or nucleic acid vaccines with high efficiency. The present invention also relates to a lipid nanoparticle (LNP) comprising the ionizable lipid compound and an active molecule, and a pharmaceutical composition comprising the lipid nanoparticle.

15 Claims, 3 Drawing Sheets

YX-30

YX-32

YX-34 a)

b)

SPLEEN-TARGETED IONIZABLE LIPID COMPOUND, COMPOSITION COMPRISING SAME AND USE THEREOF

CROSS REFERENCE TO RELATED APPLICATIONS

This application is a continuation of International Application No. PCT/CN2024/143257, filed Dec. 27, 2024, which application claims priority to Chinese Application No. 202311865464.4, filed Dec. 29, 2023, the disclosure of which are incorporated herein by reference.

TECHNICAL FIELD

The present invention provides an ionizable lipid compound, which can target spleen for delivery of biological macromolecules including nucleic acid drugs or nucleic acid vaccines with high efficiency. The present invention also relates to a lipid nanoparticle (LNP) comprising the ionizable lipid compound and an active molecule, and a pharmaceutical composition comprising the lipid nanoparticle.

BACKGROUND ART

The lipid nanoparticle (LNP) can encapsulate nucleic acid drug molecules such as RNAs and protect them from nuclease degradation, and has a high degree of stability and biocompatibility, and thus it has become a highly concerned drug delivery system in current research and development of nucleic acid drugs. The LNP is usually prepared by mixing four components, i.e. an ionizable lipid, a phospholipid, cholesterol and a PEGylated lipid at a certain ratio. The drug delivery efficiency or tissue targeting of delivery of the LNP is influenced by the ratio of constituent components of the LNP and the chemical structure of the ionizable lipid. After the LNP is administered intravenously, soluble apolipoprotein E (apoE) is usually absorbed to the surface of the LNP during blood circulation, thereby promoting the binding of the LNP to the low-density lipoprotein receptor (LDLr) highly expressed on the sinusoidal surface of liver cells, and thus the LNP can target the liver and deliver drugs. An ionizable lipid compound with an optimized hydrophobic carbon chain length and an amine head is described in Chinese patent application CN 202311261516.7 filed on Sep. 27, 2023 by the same applicant, and in this application, the inventors found that further reducing the hydrophobic carbon chain length actually increased the delivery efficiency in the liver.

Although liver-targeted delivery technologies based on LNPs have achieved rapid development, the problems of targeted and specific delivery to organs other than the liver need to be solved urgently. The spleen is the largest secondary lymphoid organ of the human body, which is widely involved in various immune functions of the body, and has a large number of antigen presenting cells and B/T lymphocytes, and thus can quickly induce a stronger immune response, and the spleen can be used as a new target for new vaccine design. However, due to the influence of the human reticuloendothelial system, after intravenous administration of drugs or LNP vehicles, most of the nanoparticles or drugs are absorbed by the liver, and the dose reaching the spleen is small, which poses a challenge to nucleic acid drug delivery and vaccine efficacy.

Therefore, the development of an LNP delivery system for spleen-targeted delivery, for example, the technology such as targeted delivery to an antigen-presenting cell (e.g., a dendritic cell (DC)) of the spleen, is of great significance for the development of nucleic acid drugs and vaccines.

SUMMARY OF THE INVENTION

The present inventors have found that an LNP comprising an ionizable lipid compound of a specific carbon chain length enables highly selective delivery of a pharmaceutically active molecule into the spleen (hereinafter sometimes also referred to as "spleen-targeted"). For this reason, the present invention is completed by the inventors of the present invention.

In a first aspect, the present invention provides a lipid compound of formula (I),

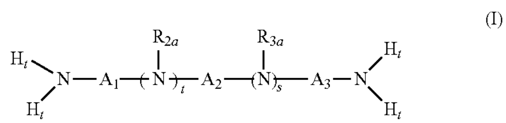

(I)

wherein $R_{2a}$ and $R_{3a}$ are each independently hydrogen, a monovalent aliphatic group, a monovalent heteroaliphatic group, a monovalent aromatic group, a monovalent heteroaromatic group, or Ht;

t and s are each independently 0 or 1, and when t or s is zero, it means that the part is directly a single bond, provided that t and s are not both 0;

$A_1$, $A_2$, and $A_3$ are each independently a single bond, a divalent aliphatic group, a divalent heteroaliphatic group, a divalent aromatic group, or a divalent heteroaromatic group, or a combination of two of the above;

each Ht is independently at each occurrence $—R_1—X—R_2—Y—R_3—Z—R_4$, wherein each $R_1$ is independently at each occurrence a divalent aliphatic group, a divalent heteroaliphatic group, a divalent aromatic group, or a divalent heteroaromatic group;

each X is independently at each occurrence

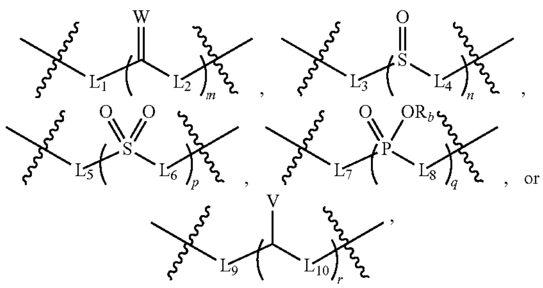

, , , or , wherein m, n, p, q, and r are each independently 1-6;

W is O, S, or $NR_c$;

$L_1$, $L_3$, $L_5$, $L_7$, and $L_9$ are directly connected to $R_1$ or $R_2$ and are each independently a single bond, O, S, or $NR_d$;

$L_2$, $L_4$, $L_6$, $L_8$, and $L_{10}$ are each independently a bond, O, S, or $NR_e$;

V is an aliphatic group, $OR_f$, $SR_g$, or $NR_hR_i$, wherein $R_b$, $R_c$, $R_d$, $R_e$, $R_f$, $R_g$, $R_h$, and $R_i$ are each independently hydrogen, hydroxyl, an oxyaliphatic group, a monovalent aliphatic group, a monovalent heteroaliphatic group, a monovalent aromatic group, or a monovalent heteroaromatic group;

Y and Z are each independently at each occurrence S or 0;

each $R_2$ is independently at each occurrence a single bond, a divalent aliphatic group, a divalent heteroaliphatic group, a divalent aromatic group, or a divalent heteroaromatic group;

each $R_3$ is independently at each occurrence a single bond, a divalent aliphatic group, a divalent heteroaliphatic group, a divalent aromatic group, or a divalent heteroaromatic group;

each $R_4$ is independently at each occurrence a hydrophobic group selected from $—(CH_2CH_2O)_y—C_1\text{-}C_2$ alkyl, $—(CH_2CH_2O)_y—C_2$ alkenyl or $—(CH_2CH_2O)_y—C_2$ alkynyl, wherein y is 0 or 1 or 2.

In some embodiments, t and s are both 0; or t is 0 and s is 1; or t is 1 and s is 0.

In some embodiments, $R_1$ is a $C_{1\text{-}6}$ (e.g., $C_{1\text{-}4}$) divalent aliphatic group or a $C_{1\text{-}6}$ (e.g., $C_{1\text{-}4}$) divalent heteroaliphatic group, preferably a $C_{1\text{-}4}$ divalent alkyl or a $C_{1\text{-}4}$ divalent heteroalkyl.

In some embodiments, X is

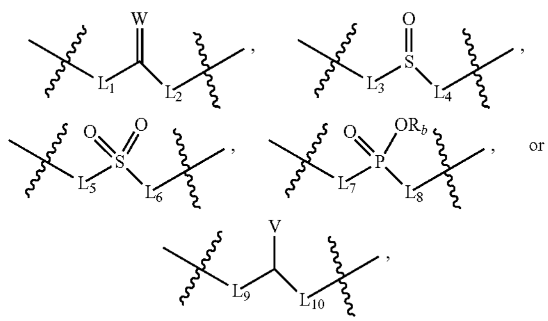

wherein each variable is as defined for formula (I). In a further embodiment, $L_1$, $L_3$, $L_5$, $L_7$, and $L_9$ are connected to $R_1$ and are each independently a single bond, O, S, or NH. In a further embodiment, X is

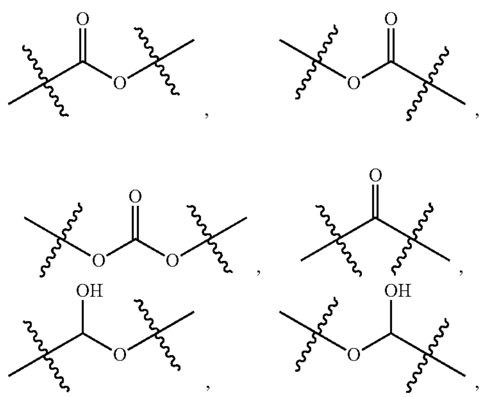

-continued

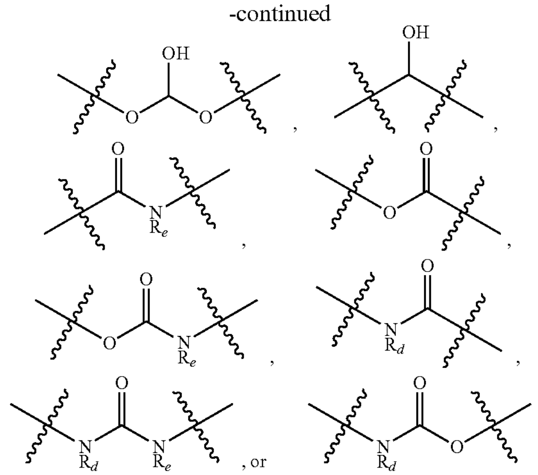

wherein $R_d$ and $R_e$ are as defined for formula (I). In some embodiments, $R^d$ and $R^e$ are each independently H or a $C_{1\text{-}4}$ monovalent aliphatic group, preferably H or $C_{1\text{-}4}$ monovalent alkyl.

In some embodiments, Y and Z are both S; or Y is S and Z is O; or Y is O and Z is S; or Y and Z are both O.

In some embodiments, each $R_2$ is independently at each occurrence a single bond or a $C_{1\text{-}6}$ divalent aliphatic group (e.g., a $C_{1\text{-}4}$ divalent aliphatic group, preferably a $C_{1\text{-}4}$ divalent alkyl, more preferably a $C_1$-2 divalent alkyl).

In some embodiments, each $R_3$ is independently at each occurrence a single bond or a $C_{1\text{-}6}$ divalent aliphatic group (e.g., a $C_{1\text{-}4}$ divalent aliphatic group, preferably a $C_{1\text{-}4}$ divalent alkyl). In a further embodiment, each $R_3$ is independently at each occurrence a single bond, or

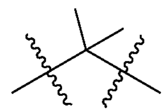, or methylene (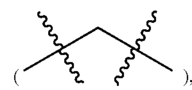), preferably

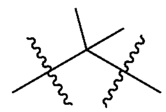.

In some embodiments, each $R_4$ is independently at each occurrence ethyl ($C_2H_5$), methyl ($CH_3$), ethenyl, ethynyl, $—(CH_2CH_2O)—CH_3$, $—(CH_2CH_2O)—C_2H_5$, $—(CH_2CH_2O)—CH{=}CH_2$, $—(CH_2CH_2O)—C{\equiv}CH$, $—(CH_2CH_2O)_2—CH_3$, $—(CH_2CH_2O)_2—C_2H_5$, $—(CH_2CH_2O)_2—CH{=}CH_2$ or $—(CH_2CH_2O)_2—C{\equiv}CH$.

In some embodiments, each Ht is independently at each occurrence

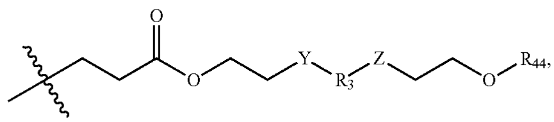

wherein Y and Z are both S; or Y is S and Z is O; or Y is O and Z is S; or Y and Z are both O; each $R_3$ is independently at each occurrence a single bond or

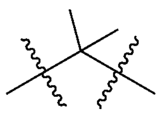 [SMILES: *C(*)(C)C]

or methylene

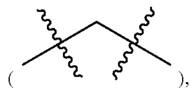

and $R_{44}$ is ethyl ($C_2H_5$), methyl ($CH_3$), ethenyl or ethynyl.

In the present invention, $A_1$, $A_2$ and $A_3$ form an amine head of the lipid compound, which undergoes an addition reaction with a hydrophobic lipid tail to obtain a series of lipid compounds. Since the amine head can be protonated, such lipid compound nanoparticles are positively charged as a whole, so they can undergo an electrostatic interaction with negatively charged mRNAs, cell membranes and lysosomal membranes, such that such lipid compounds can effectively encapsulate and deliver mRNAs. In some embodiments, the pKa value of the amine head is greater than 4, preferably greater than 6, and more preferably greater than 8.

In some embodiments, t is 1, s is 0, $A_2$ is a single bond, and $A_1$ and $A_3$ are each independently a divalent aliphatic group or a divalent heteroaliphatic group; in a further embodiment, $A_1$ and $A_3$ are each independently a $C_1$-$C_6$ divalent aliphatic group (e.g., a $C_1$-$C_4$ divalent aliphatic group, preferably $C_1$-$C_4$ divalent alkyl); and in a further embodiment, $A_1$ and $A_3$ are each independently $-CH_2CH_2-$ or $-CH_2CH_2CH_2-$, and $R_{2a}$ is hydrogen or a monovalent aliphatic group, or is hydrogen or $C_1$-$C_6$ alkyl or methyl. In some embodiments, t is 1, s is 1, $A_1$, $A_2$ and $A_3$ are each independently a divalent aliphatic group or a divalent heteroaliphatic group; in a further embodiment, $A_1$, $A_2$ and $A_3$ are each independently a $C_1$-$C_6$ divalent aliphatic group (e.g., a $C_1$-$C_4$ divalent aliphatic group, preferably $C_1$-$C_4$ divalent alkyl); and in a further embodiment, $A_1$, $A_2$ and $A_3$ are each independently $-CH_2CH_2-$ or $-CH_2CH_2CH_2-$, and $R_{2a}$ and $R_{3a}$ are each independently hydrogen or a monovalent aliphatic group, or is hydrogen or $C_1$-$C_6$ alkyl or methyl.

In some embodiments,

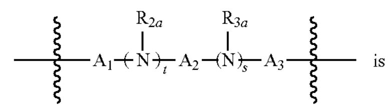

is

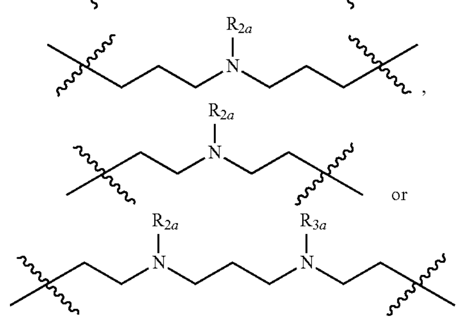

wherein $R_{2a}$ and $R_{3a}$ are each independently hydrogen or a monovalent aliphatic group, or hydrogen or $C_1$-$C_6$ alkyl or methyl.

In some embodiments, the lipid compound of formula (I) is

YX-30

YX-32

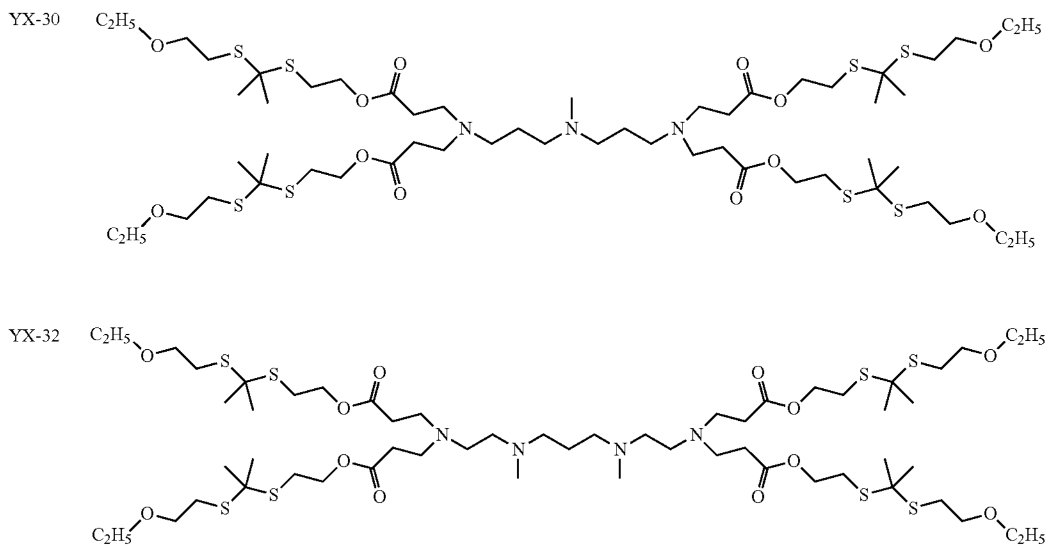

-continued

YX-34

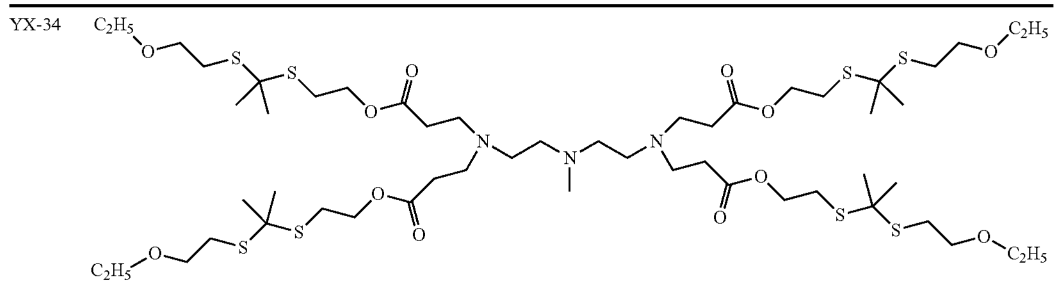

In a second aspect, the present invention provides a method for preparing a lipid compound of formula (I) in which $R_1$ is ethylene, the method comprising:

mixing and reacting an acrylic compound of formula (II), i.e. $CH_2{=}CH{-}X{-}R_2{-}Y{-}R_3{-}Z{-}R_{41}$ (II), in which each variable is as defined for formula (I), with a hydrophilic amine at a molar ratio, wherein the molar ratio of the hydrophilic amine to the acrylate compound of formula (II) is greater than 4, for example 4.3:1 or 4.5:1, to ensure that the reaction is fully completed; and then optionally, purifying the product by column chromatography to obtain the desired lipid compound of formula (I);

wherein the variables $R_2$, X, Y, $R_3$, Z, and $R_4$ are as defined for formula (I). In some embodiments, X is

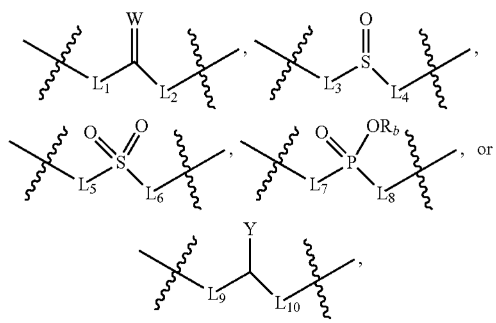

wherein each variable is as defined for formula (I). In a further embodiment, $L_1$, $L_3$, $L_5$, $L_7$, and $L_9$ are connected to $R_1$ and are each independently a single bond, O, S, or NH. In a further embodiment, X is

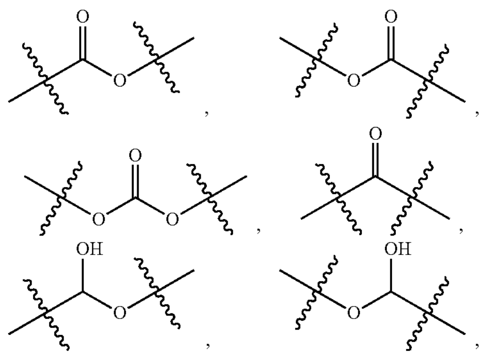

-continued

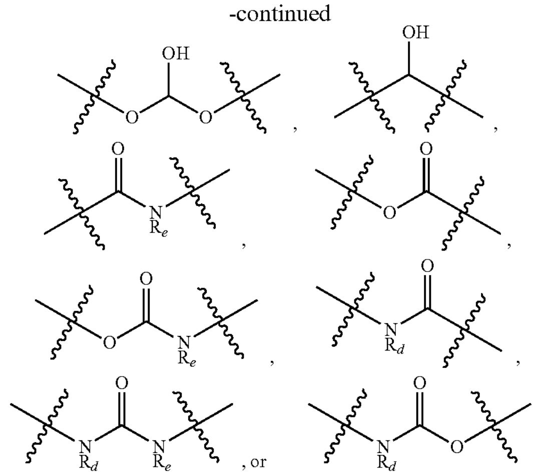

wherein $R_d$ and $R_e$ are as defined for formula (I). In some embodiments, $R^d$ and $R^e$ are each independently H or a $C_{1-4}$ monovalent aliphatic group, preferably H or $C_{1-4}$ monovalent alkyl.

In some embodiments, in method (a), the product is purified by column chromatography to obtain the desired lipid compound of formula (I), wherein the column chromatographic purification method is well known in the art.

In some embodiments, in the present invention, $A_1$, $A_2$ and $A_3$, together with the N to which they are attached, form an amine head of the lipid compound, which undergoes an addition reaction with a hydrophobic lipid tail to obtain a series of lipid compounds. Since the amine head can be protonated, such lipid compound nanoparticles are positively charged as a whole, so they can undergo an electrostatic interaction with negatively charged mRNAs and cell membranes, such that such lipid compounds can effectively encapsulate and deliver mRNAs.

In some embodiments, the hydrophilic amine in the method is selected from

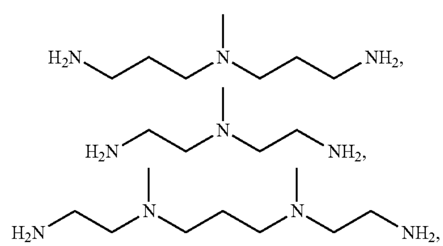

-continued

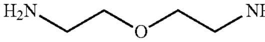, 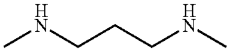,

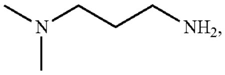, 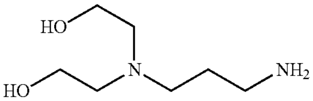,

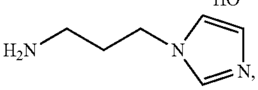, 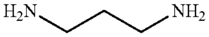,

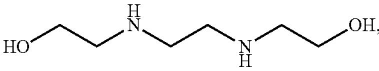,

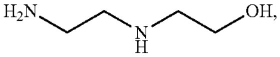,

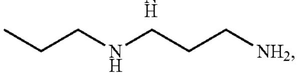,

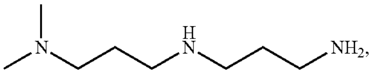,

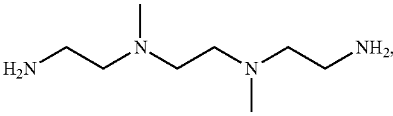,

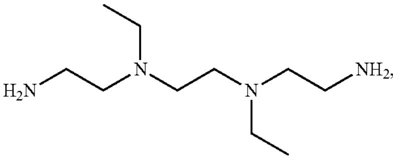,

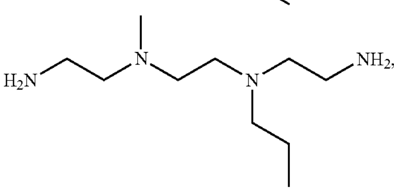,

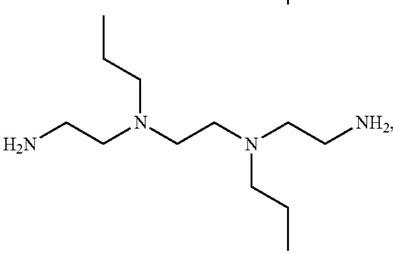,

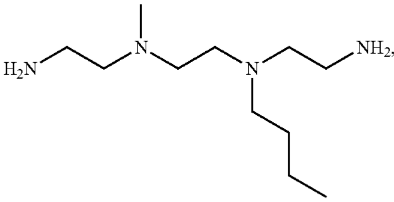,

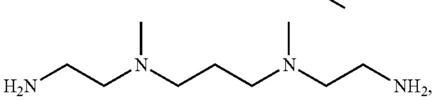,

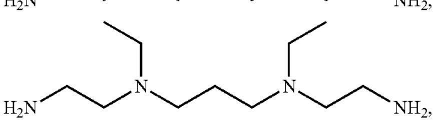,

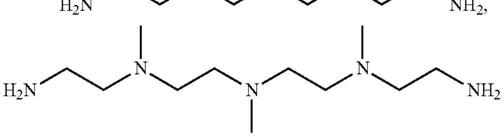 or

-continued

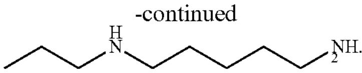.

In some embodiments, the ketal-containing acrylate $CH_2{=}CH{-}C(O)O{-}R_2{-}Y{-}R_3{-}Z{-}R_4$ is

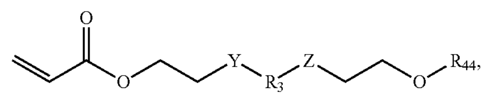

and the remaining variables are as defined for formula (I).

In some embodiments, the reaction is an addition reaction, preferably a Michael addition reaction.

In some embodiments, the reaction is carried out at a temperature of 60° C.-85° C., such as at 70° C. for 24-96 hours or longer.

The ketal-containing acrylate described in the present invention can be synthesized according to a method known in the art, such as a method disclosed in CN 110101665 A. The ketal (thioketone)-containing acrylate is an ester compound obtained by subjecting an acrylic acid and an alcohol compound containing ketal (thioketone) to an esterification reaction.

Other lipid compounds of the present invention can be prepared by the above synthesis routes and other routes known in the art using other suitable starting materials. The methods listed above may include one or more additional steps to add or remove appropriate protecting groups to finally allow for the synthesis of lipid compounds. In addition, various synthesis steps can be carried out in an alternative order or sequence to obtain the desired materials. Synthetic chemical transformation and protective group methods (protection and deprotection) which can be used to synthesize suitable lipid compounds are known in the art.

In a third aspect, the present invention provides a pharmaceutical composition comprising a pharmaceutical carrier and a lipid nanoparticle (LNP), wherein the lipid nanoparticle comprises the lipid compound of formula (I) according to the present invention and a pharmaceutically active molecule.

In some embodiments, the pharmaceutically active molecule target the spleen as a target organ. In some embodiments, the pharmaceutical active molecule is a nucleic acid, an antigen, a vaccine, an immunomodulator, or another active ingredient, or a combination thereof, that targets the spleen as a target organ. In some embodiments, the pharmaceutically active molecule is an mRNA. In still a further embodiment, the mRNA may be a firefly luciferase mRNA which can be expressed as luciferase.

In some embodiments, the lipid nanoparticle has a particle size distribution of about 50 to about 500 nm.

In some embodiments, the lipid compound and the pharmaceutically active molecule are bound via a non-covalent interaction, a covalent bond or both.

In some embodiments, the lipid nanoparticle further comprises other lipids, such as phospholipids, cholesterol, and PEGylated lipids, i.e., lipids conventionally used to form LNPs. In the LNP of the present invention, the molar ratio of the lipid compound to cholesterol to phospholipid to PEGylated lipid is (about 15 to about 50):(about 38.5 to about 75):(about 10 to about 25):(about 0.5 to about 3). In some embodiments, the molar ratio of the lipid compound: cholesterol:phospholipid:PEGylated lipid is about 50:about 38.5:about 10:about 1.5. In some embodiments, the molar ratio of the lipid compound:cholesterol:phospholipid:PEGylated lipid is about 25:about 48.5:about 25:about 1.5. In some embodiments, the molar ratio of the lipid compound: cholesterol:phospholipid:PEGylated lipid is about 15:about 74.5:about 10:about 0.5. In some embodiments, the molar ratio of the lipid compound:cholesterol:phospholipid:PEGylated lipid is about 20:about 60:about 19.5:about 0.5. In some embodiments, the molar ratio of the lipid compound: cholesterol:phospholipid:PEGylated lipid is about 25:about 65:about 9.5:about 0.5. In some embodiments, the molar ratio of the lipid compound:cholesterol:phospholipid:PEGylated lipid is about 30:about 60:about 9.5:about 0.5. In some embodiments, the N/P ratio of the lipid compound to the nucleic acid ranges from about 5:1 to about 20:1. In some embodiments, the N/P ratio of the lipid compound to the nucleic acid ranges from about 7:1 to about 15:1. In some embodiments, the N/P ratio of the lipid compound to the nucleic acid is about 6:1, about 7.5:1 or about 9:1.

In some embodiments, the PEGylated lipid refers to a lipid modified with polyethylene glycol (PEG). Hydrophilic PEG stabilizes LNPs, modulates nanoparticle size, and increases the half-life of nanoparticles by reducing non-specific interaction with macrophages. In some embodiments, the PEGylated lipid is selected from PEG-modified phosphatidylethanolamine, PEG-modified phosphatidic acid, PEG-modified ceramide, PEG-modified dialkylamine, PEG-modified diacylglycerol, PEG-modified dialkylglycerol, or any combination thereof. The molecular weight of PEG in PEG modifications is typically 350-5000 Da. In some embodiments, the PEGylated lipid is selected from distearoyl phosphatidylethanolamine-polyethylene glycol 2000 (DSPE-PEG2000), 1,2-dimyristoyl-RAC-glycero-3-methoxypolyethylene glycol 2000 (DMG-PEG2000), and methoxy polyethylene glycol ditetradecylacetamide (ALC-0159).

In some embodiments, the phospholipid is selected from phosphatidylcholine, phosphatidylethanolamine, phosphatidylglycerol, phosphatidylserine, phosphatidic acid, 2-lysophosphatidylcholine, and sphingomyelin. The fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. In some embodiments, the phospholipid is selected from 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterol hemisuccinyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyloleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-stearoylethanolamine (SOSE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE) and a mixture thereof.

In some embodiments, the lipid nanoparticles of the present invention are prepared by the method comprising: dissolving the ionizable lipid compound of the present invention, cholesterol, DOPE and DSPE-PEG2000 in absolute ethanol respectively, and dissolving the pharmaceutically active molecule (the mass of lipid compounds being 5-20 times the mass thereof (the N/P ratio of lipid compounds to nucleic acids being in the range of about 5:1 to about 20:1)) in 100 mM sodium acetate buffer (pH=about 5.2). The ethanol solution and the sodium acetate buffer solution were mixed and prepared on a microfluidic machine at a flow rate of 1:3. In a further embodiment, the pharmaceutically active molecule is an mRNA.

The present invention also relates to a method for delivering an antigen to an antigen presenting cell (preferably a professional antigen presenting cell, such as a dendritic cell and/or a macrophage) of the spleen or expressing an antigen in an antigen presenting cell (preferably a professional antigen presenting cell, such as a dendritic cell and/or a macrophage) of the spleen, comprising administering a pharmaceutical composition of the present invention to a subject in need thereof.

The present invention also relates to a method for inducing an immune response (preferably an immune response against cancer), in a subject, comprising administering a pharmaceutical composition of the present invention to a subject in need thereof.

The present invention also relates to a method for treating a disease caused by spleen damage or abnormalities, comprising administering the pharmaceutical composition of the present invention to a subject in need thereof. In some embodiments, the disease caused by spleen damage or abnormalities comprises lymphoma, leukemia, and the like.

Definitions

The term "aliphatic group" refers to a saturated or unsaturated, linear or branched, acyclic, cyclic or polycyclic hydrocarbon moiety. Examples include, but are not limited to, alkyl, alkenyl, alkynyl, cycloalkyl, cycloalkenyl, and cycloalkynyl moieties.

The term "alkyl" includes hydrocarbon groups selected from linear and branched saturated hydrocarbon groups containing 1 to 30, such as 1 to 24, 1 to 18, such as 1 to 12, further such as 1 to 10, and still further such as 1 to 8 or 1 to 6 or 1 to 4 carbon atoms. Examples of monovalent alkyl or alkyl include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, triacontyl, etc. Examples of divalent alkyl, i.e. alkylene, include, but are not limited to, methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, triacotylene, etc.

A monovalent group is a group formed by removing a hydrogen atom from the corresponding hydrocarbon moiety. A divalent group is a group formed by removing two hydrogen atoms from the corresponding hydrocarbon moiety.

The term "alkenyl" includes hydrocarbon groups selected from linear and branched hydrocarbon groups containing at least one C═C double bond and 2 to 30, such as 2 to 24, 2 to 18, such as 2 to 8, further such as 2 to 6 carbon atoms. Examples of alkenyl, such as $C_{2-6}$ alkenyl, include, but are not limited to, ethenyl/vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, hexa-1,3-dienyl, dodecenyl, tetradecenyl, hexadecenyl, octadecenyl, etc.

The term "alkynyl" includes hydrocarbon groups selected from linear and branched hydrocarbon groups containing at least one C≡C triple bond and 2 to 30, such as 2 to 24, 2 to 18, such as 2 to 8, further such as 2 to 6 carbon atoms. Examples of alkynyl, such as $C_{2-6}$ alkynyl, include but are not limited to ethynyl, 1-propynyl, 2-propynyl (propargyl), 1-butynyl, 2-butynyl, and 3-butynyl.

The term "cycloalkyl" includes hydrocarbon groups selected from saturated cyclic hydrocarbon groups containing monocyclic and polycyclic (e.g., bicyclic and tricyclic) groups, including fused, bridged or spirocyclic alkyl. The cycloalkyl may contain 3 to 30, 3 to 12, for example 3 to 10, further for example 3 to 8, further for example 3 to 6, 3 to 5 or 3 to 4 carbon atoms. Furthermore, by way of example, the cycloalkyl may be selected from monocyclic groups containing 3 to 12, such as 3 to 10, further such as 3 to 8, 3 to 6 carbon atoms. Examples of monocyclic cycloalkyl include cyclopropyl, cyclobutyl, cyclopentyl, cyclohexyl, cycloheptyl, cyclooctyl, cyclononyl, cyclodecyl, cycloundecyl, and cyclododecyl. The term "cycloalkenyl" refers to a non-aromatic, cyclic hydrocarbon moiety containing at least one double bond, such as cyclohexenyl and cyclohexenylene. The term "cycloalkynyl" refers to a non-aromatic, cyclic hydrocarbon moiety containing at least one triple bond, such as cyclooctynyl and cyclooctynylene. Similarly, cycloalkylene, cycloalkenylene, and cycloalkynylene are corresponding divalent groups.

The term "heteroaliphatic group" refers to an aliphatic moiety containing at least one heteroatom selected from N, O, P, B, S, Si, Sb, Al, Sn, As, Se, and Ge. The heteroaliphatic group of the present invention includes alkyl, alkenyl or alkynyl containing at least one heteroatom selected from N, O, P, B, S, Si, Sb, Al, Sn, As, Se, and Ge, and a cycloalkyl, cycloalkenyl or cycloalkynyl moiety containing at least one heteroatom selected from N, O, P, B, S, Si, Sb, Al, Sn, As, Se, and Ge. The cyclic heteroaliphatic group includes a 3- to 7-membered monocyclic heteroaliphatic group and a 7- to 12-membered bicyclic heteroaliphatic group, and the cyclic heteroaliphatic groups contain 1-3 or more, for example, 1-3 heteroatoms selected from oxygen, nitrogen and sulfur. In some embodiments, the cyclic heteroaliphatic group is a 3- to 7-membered monocyclic heteroaliphatic group containing 1-3 heteroatoms selected from oxygen, nitrogen and sulfur. Cyclic heteroaliphatic groups include, but are not limited to, pyrrolidinyl, imidazolidinyl, piperidinyl, piperazinyl, pyranyl, morpholinyl, oxiranyl, azirinyl, thiiranyl, azetidinyl, oxetanyl, thietanyl, dithietanyl, dihydropyridine, tetrahydropyridine, thiomorpholine, homopiperazinyl, homopiperidinyl, azepanyl, oxepanyl, thiepanyl, oxathianyl, dioxepanyl, oxathiepanyl, oxazepanyl, dithiepanyl, thiazepanyl, diazepanyl, thiazinanyl, oxazepine, diazepine, thiazepine, dihydrothienyl, dihydropyranyl, dihydrofuranyl, tetrahydrofuranyl, tetrahydrothienyl, tetrahydropyranyl, tetrahydrothiapyranyl, pyrrolinyl, indolinyl, dioxanyl, dioxolanyl, pyrazolinyl, pyrazolidinyl, dithianyl, dithiolanyl, pyrimidonyl, dioxo-thiomorpholinyl, azabicyclo[3.1.0]hexyl, azabicyclo[4.1.0]heptyl, azabicyclo[2.2.2]hexyl, etc. A typical heteroaliphatic group is heteroalkyl, i.e. an alkyl group containing at least one heteroatom such as N, O or S, e.g. $C_{1-6}$ alkyl containing one N atom, $C_{1-6}$ alkyl containing one O atom, or $C_{1-6}$ alkyl containing one S atom; or $C_{1-4}$ heteroalkyl containing one N atom, $C_{1-4}$ heteroalkyl containing one O atom, or $C_{1-4}$ heteroalkyl containing one S atom.

The term "oxyaliphatic group" refers to a —O-aliphatic group. Examples of the oxyaliphatic group include methoxy, ethoxy, n-propoxy, isopropoxy, n-butoxy, isobutoxy, sec-butoxy, and tert-butoxy.

The term "aryl (aromatic group)" refers to a C6 monocyclic, C10 bicyclic, C14 tricyclic, C20 tetracyclic, or C24 pentacyclic aromatic ring system. Examples of aryl include phenyl, phenylene, naphthyl, naphthylene, anthryl, anthrylene, pyrenyl, and pyrenylene.

The term "heteroaryl (heteroaromatic group)" refers to aromatic 5- to 8-membered monocyclic, 8- to 12-membered bicyclic, 11- to 14-membered tricyclic, and 15- to 20-membered tetracyclic ring systems having one or more heteroatoms (such as O, N, S, or Se). Examples of heteroaryl include furanyl, furanylene, fluorenyl, fluorenylene, pyrrolyl, pyrrolylene, thienyl, thienylene, oxazolyl, azolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolinyl, isoquinolinylene, indolyl, and indolylene.

Unless otherwise specified, the aliphatic group, heteroaliphatic group, oxyaliphatic group, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned in the present application include both substituted and unsubstituted moieties. Possible substituents on the cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_2$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamido, arylsulfonamido, $C_1$-$C_{10}$ alkylimino, arylimino, $C_1$-$C_{10}$ alkylsulfonimido, arylsulfonimido, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylate. In another aspect, possible substituents on the aliphatic group, heteroaliphatic group, oxyaliphatic group, alkyl, alkylene, alkenyl, alkenylene, alkynyl, and alkynylene include all the substituents listed above, except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl may also be fused with one another.

The term "pharmaceutically active molecule" refers to any chemical substance intended for medical diagnosis, cure, treatment or prevention of diseases. In some embodiments, the pharmaceutically active molecule target the spleen as a target organ. In some embodiments, the pharmaceutical active molecule is a nucleic acid, an antigen, a vaccine, an immunomodulator, or another active ingredient, or a combination thereof, that targets the spleen as a target organ. In some embodiments, the antigen is an antigenic peptide or protein derived from a pathogenic antigen, a tumor antigen, an allergic antigen, or an autoimmune autoantigen. In some embodiments, the vaccine is a tumor vaccine, an influenza vaccine, or a rabies vaccine.

The term "RNA" or "nucleic acid" comprises a nucleic acid molecule of ribonucleotide residues or a nucleic acid molecule with chemically modified bases. In some embodiments, the RNA comprises all or most of the ribonucleotide residues.

The term "ribonucleotide" refers to a nucleotide having a hydroxyl group at the 2'-position of the β-D-ribofuranosyl group.

The RNA includes, but is not limited to, a double-stranded RNA, a single-stranded RNA, an isolated RNA (for example, a partially purified RNA), a substantially pure RNA, a synthetic RNA, an RNA produced by recombination, and a modified RNA different from a naturally occurring RNA by additions, deletions, substitutions and/or alterations of one or more nucleotides. In some embodiments, the RNA is a messenger RNA (mRNA) associated with an RNA transcript encoding a peptide or protein. As recognized in the art, an mRNA typically comprises a 5'-untranslated region (5'-UTR), a peptide coding region, and a 3'-untranslated region (3'-UTR). In some embodiments, the RNA is produced by in vitro transcription or chemical synthesis. In some embodiments, the mRNA is produced by in vitro transcription using a DNA template, wherein the DNA refers to a nucleic acid comprising deoxyribonucleotides. In some embodiments, the RNA is an in vitro transcribed RNA (IVT RNA) and can be obtained by in vitro transcription using a suitable DNA template.

In some embodiments, the concentration of RNA in the present pharmaceutical composition comprising the LNP is about 0.01 mg/mL to about 1 mg/mL, or about 0.05 mg/mL to about 0.5 mg/mL. In some specific embodiments, the concentration of the RNA is about 0.05 mg/mL, about 0.06 mg/mL, about 0.07 mg/mL, about 0.08 mg/mL, about 0.09 mg/mL, about 0.10 mg/mL, about 0.11 mg/mL, about 0.12 mg/mL, about 0.13 mg/mL, about 0.14 mg/mL, about 0.15 mg/mL, about 0.16 mg/mL, about 0.17 mg/mL, about 0.18 mg/mL, about 0.19 mg/mL, about 0.20 mg/mL, about 0.21 mg/mL, about 0.22 mg/mL, about 0.23 mg/mL, about 0.24 mg/mL, about 0.25 mg/mL, about 0.26 mg/mL, about 0.27 mg/mL, about 0.28 mg/mL, about 0.29 mg/mL, about 0.30 mg/mL, about 0.31 mg/mL, about 0.32 mg/mL, about 0.33 mg/mL, about 0.34 mg/mL, about 0.35 mg/mL, about 0.36 mg/mL, about 0.37 mg/mL, about 0.38 mg/mL, about 0.39 mg/mL, about 0.40 mg/mL, about 0.41 mg/mL, about 0.42 mg/mL, about 0.43 mg/mL, about 0.44 mg/mL, about 0.45 mg/mL, about 0.46 mg/mL, about 0.47 mg/mL, about 0.48 mg/mL, about 0.49 mg/mL or about 0.50 mg/mL.

In some embodiments, when the LNP is administered systemically, the LNP targets to the spleen or accumulates in the spleen. Preferably, when the LNP is administered systemically, the LNP delivers an RNA to an antigen presenting cell of the spleen, preferably a professional antigen presenting cells, such as a dendritic cell and/or macrophage. In some embodiments, the LNP releases the RNA at a target organ or target tissue and/or enters a cell of the target organ or target tissue. In some embodiments, the target organ or target tissue is targeted lymphatic system, particularly a secondary lymphoid organ, more particularly the spleen, and the cell at the target organ or target tissue is an antigen presenting cell, such as a dendritic cell. In some embodiments, after systemic administration of the LNP, the RNA expression occurs in an antigen presenting cell of the spleen, in a professional antigen presenting cell. In some embodiments, the RNA expression occurs in the spleen following systemic administration of the LNP of the present invention. In some embodiments, when the LNP is administered systemically, the LNP does not target or substantially does not target the lung and/or liver, or does not accumulate or substantially does not accumulate in the lung and/or liver. In some embodiments, the RNA expression substantially does not occur in the lung and/or liver following systemic administration of the LNP of the present invention. In some embodiments, the amount of nanoparticles targeting to or accumulating in the spleen is at least 5 times, preferably at least 8 times, preferably at least 10 times, preferably at least 20 times, preferably at least 50 times, preferably at least 100 times, preferably at least 1000 times or even higher than the amount of nanoparticles targeting to the lung or accumulating in the lung. In some embodiments, the RNA expression level in the spleen is at least 5 times, at least 8 times, at least 10 times, at least 20 times, at least 50 times, at least 100 times, preferably at least 1000 times or even higher than the RNA expression level in the liver following systemic administration of the LNP.

The antigen encoded by the RNA contained in the LNP described in the present application is preferably a disease-associated antigen, or the antigen elicits an immune response against the disease-associated antigen or against the cell expressing the disease-associated antigen.

The pharmaceutical composition of the present invention may further comprise one or more pharmaceutically acceptable carriers, diluents and/or excipients. The pharmaceutical composition of the present invention may further comprise at least one adjuvant.

The pharmaceutical compositions of the present application may be administered by a conventional route, such as by parenteral administration, including by injection or infusion. In some embodiments, the pharmaceutical composition of the present invention is administered parenterally, e.g., intravenously, intraarterially, subcutaneously, intradermally, or intramuscularly. The term "parenteral administration" refers to administration in a manner that does not pass through the digestive tract, such as intravenous or intramuscular injection. Systemic administration (also known as whole-body administration) is a route of administration that includes enteral administration (i.e., administration involving absorption through the gastrointestinal tract) or parenteral administration. The pharmaceutical composition of the present invention may be formulated for systemic administration.

The pharmaceutical composition of the present invention is useful for inducing an immune response, particularly an immune response against a disease-associated antigen or a cell expressing a disease-associated antigen, such as an immune response against cancer. Accordingly, the pharmaceutical composition may be used for the prophylactic and/or therapeutic treatment of a disease involving a disease-associated antigen or a cell expressing a disease-associated antigen, such as cancer. In some embodiments, the disease-associated antigen is a tumor antigen.

The term "subject" or "patient" in the present application includes humans and mammals.

The term "therapeutically effective amount" is an amount of a therapeutic agent that, when administered to a patient, may ameliorate a disease or symptom. A "prophylactically effective amount" is an amount of a prophylactic agent that, when administered to a subject, may prevent a disease or symptom. The amount of a therapeutic agent that constitutes the "therapeutically effective amount" or the amount of a prophylactic agent constitutes the "prophylactically effective amount" varies with the therapeutic/prophylactic agent itself, the disease state and its severity, the age and body weight of the patient/subject to be treated/in need of prevention, and the like. The therapeutically effective amount and the prophylactically effective amount can be conventionally determined by one of ordinary skill in the art based on his knowledge and the present disclosure.

The term "pharmaceutically acceptable" as used herein means that the compound or composition is chemically and/or toxicologically compatible with other ingredients constituting the preparation, and/or is compatible with the human or mammal for whom the compound or composition is used to prevent or treat a disease or condition.

The term "treatment", as used in the present application, refers to the administration of one or more drug substances to a patient or subject suffering from a disease or having symptoms of the disease, in order to cure, relieve, alleviate, ameliorate or affect the disease or symptoms of the disease. In the context of the present application, unless specifically stated to the contrary, the term "treatment" may also include prophylaxis.

DETAILED DESCRIPTION OF EMBODIMENTS

Figure 1:
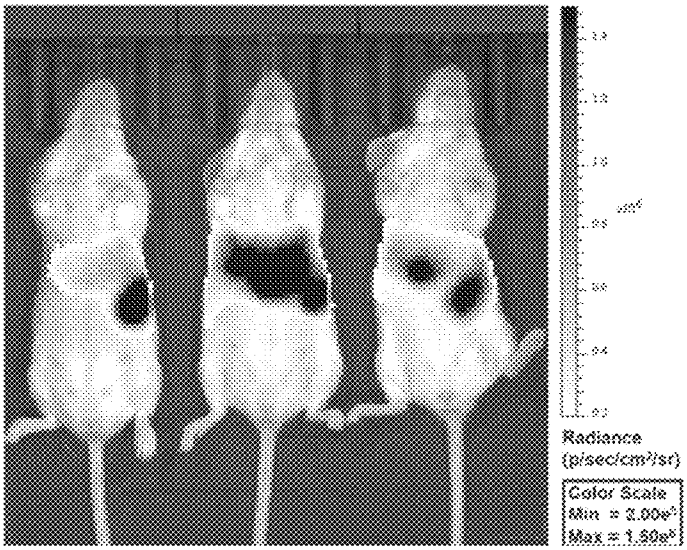
FIG. 1 shows in vivo bioluminescence imaging images after delivery of Firefly luciferase (Fluc) mRNAs by LNPs prepared from lipid compounds YX-30, YX-32 and YX-34 (administered dose: 150 μg/kg).
Figure 1:
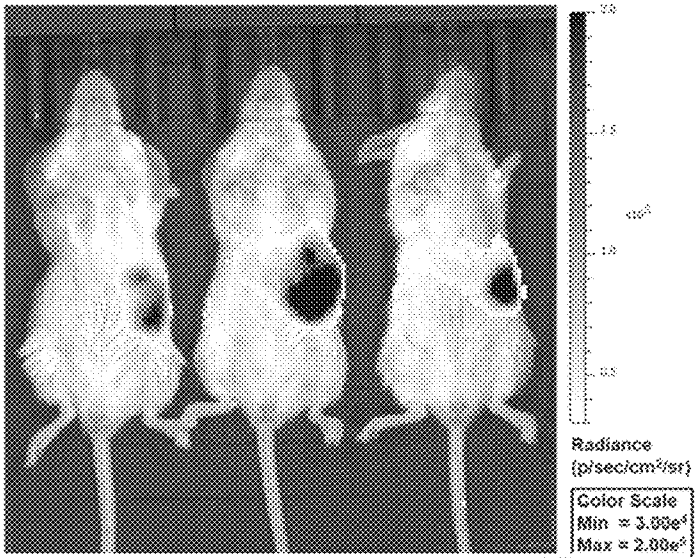
Figure 1:
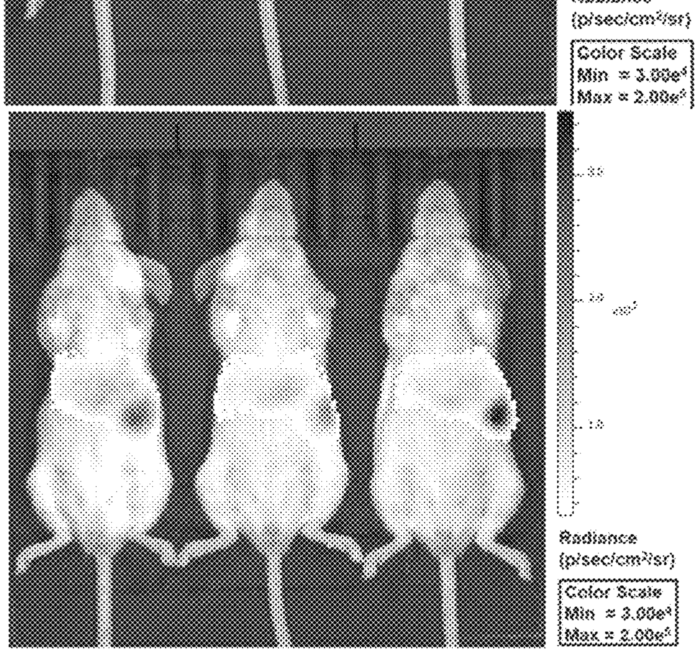

The present invention will be further described in detail in conjunction with specific embodiments, and examples are given only to illustrate the present invention, but not to limit the scope of the present invention. The examples provided below can be used as a guide for further improvement by those of ordinary skill in the art and are not intended to limit the present invention in any way.

For all the quantitative experiments in the following examples, three repeated experiments are set up and the results are averaged.

The experimental methods in the following examples are all conventional unless otherwise specified. The materials, reagents, etc., used in the following examples can all be obtained from commercial sources unless otherwise specified.

In the following examples, cholesterol is a product from Macklin, with article number C10006595, CAS: 57-88-5.

In the following examples, both DOPE (dioleoylphosphatidylethanolamine, CAS: 4004-05-1) and DMG-$PEG_{2000}$ (CAS: 147867-65-) are products from Aveto (Shanghai) Pharmaceutical Technology Co., Ltd.

The firefly luciferase mRNA in the following examples is a product from Shanghai Hongene Technology Development Co., Ltd.

In the following examples, Balb/c mice are products from Beijing Vital River Laboratory Animal Technology Co., Ltd.

Example 1: Synthesis of Ionizable Lipid Compounds

The cationizable lipid compound is synthesized from the corresponding hydrophilic amine compound and the ketal-containing acrylate TK2 by Michael addition reaction.

The hydrophobic tail molecule TK2, i.e. 2-((2-((2-(ethyloxy)ethyl)thio)propan-2-yl)thio)ethyl acrylate

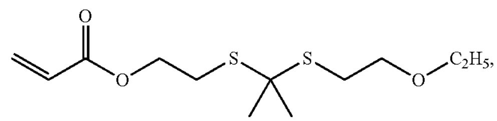 [SMILES: C=CC(=O)OCCSC(C)(C)SCCOCC]

was synthesized in a similar manner to that in Examples 1 and 2 in CN110101665A. Specifically,

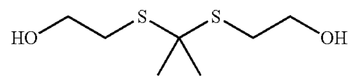

2,2'-(propane-2,2-diylbis(sulfanediyl))bis(ethan-1-ol) and the corresponding haloethane (e.g., bromoethane) were used as starting materials, to prepare

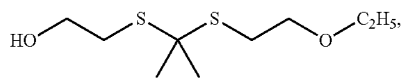

which was then reacted with an acrylyl halide (e.g., acryloyl chloride) to obtain TK2.

$^1$H NMR of TK2 was as follows: $^1$H NMR (300 MHz, $CDCl_3$) δ 6.41 (d, 1H), 6.12 (t, 1H), 5.83 (d, 1H), 4.32 (d, 2H), 3.59 (d, 2H), 3.46 (d, 2H), 2.92 (d, 2H), 2.82 (d, 2H), 1.61-1.38 (m, 10H), 0.89 (d, 3H).

YX-30 was synthesized from hydrophilic amine compound N,N-di(3-aminopropyl)methylamine and TK2, wherein the hydrophilic amine compound N,N-di(3-aminopropyl)methylamine and TK2 were mixed at a molar ratio of 4.3:1 and heated at 70° C. for 72 h. The crude product was purified on a silica gel column with dichloromethane/methanol as an eluent to obtain cationizable lipid compound YX-30. $^1$H NMR of YX-30 was as follows: $^1$H NMR (300 MHz, $CDCl_3$) δ 4.22 (t, 8H), 3.59-3.50 (m, 16H), 2.86-2.77 (m, 24H), 2.45 (t, 12H), 2.28 (t, 4H), 2.18 (s, 3H), 1.60 (s, 32H), 1.20 (t, 12H).

YX-32 and YX-34 were synthesized from the corresponding hydrophilic amine compounds 2,2'-diamino-N-methyldiethylamine and N,N'-bis(2-aminoethyl)-N,N'-dimethyl-1,3-propanediamine, respectively, and TK2, according to the above method.

YX-32: $^1$H NMR (300 MHz, $CDCl_3$) δ 4.22 (t, 8H), 3.60 (t, 8H), 3.52 (t, 8H), 2.88-2.77 (m, 24H), 2.47 (t, 8H), 1.60 (s, 24H), 1.25-1.18 (m, 20H), 1.10 (t, 12H)

YX-34: $^1$H NMR (300 MHz, $CDCl_3$) δ 4.22 (t, 8H), 3.58 (t, 8H), 3.44 (t, 8H), 2.86-2.77 (m, 24H), 2.55-2.46 (m, 16H), 2.23 (s, 3H), 1.60-1.38 (m, 26H), 1.20 (t, 12H).

allowed to reach 450 μL by supplementing ethanol. 150 g of firefly luciferase mRNAs were taken and added to a sodium acetate buffer (50 mM, pH=5.2), and the total volume of the

YX-30

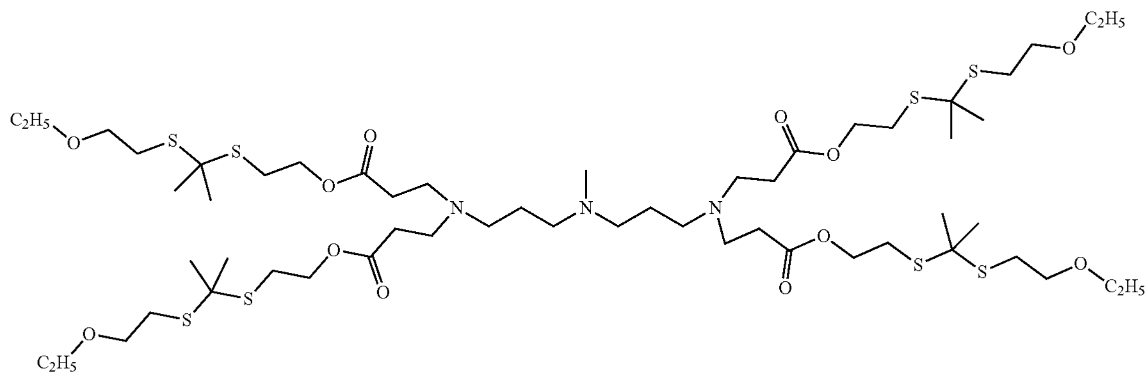

YX-32

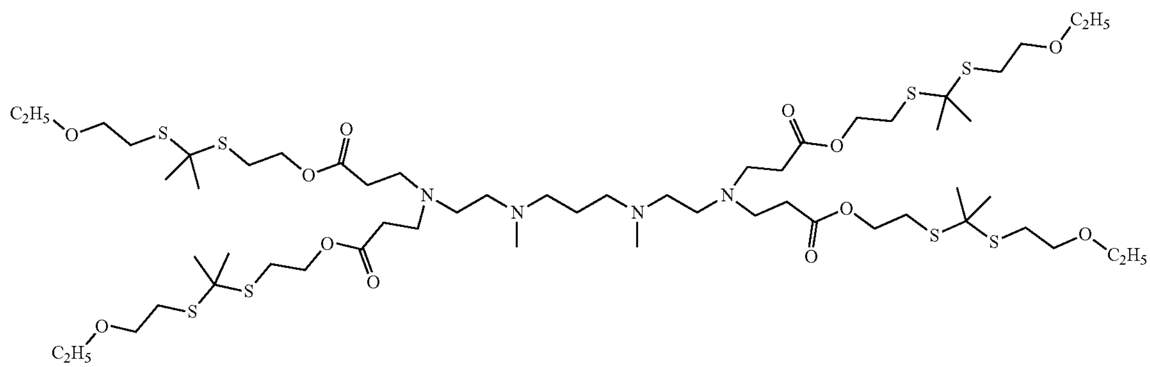

YX-34

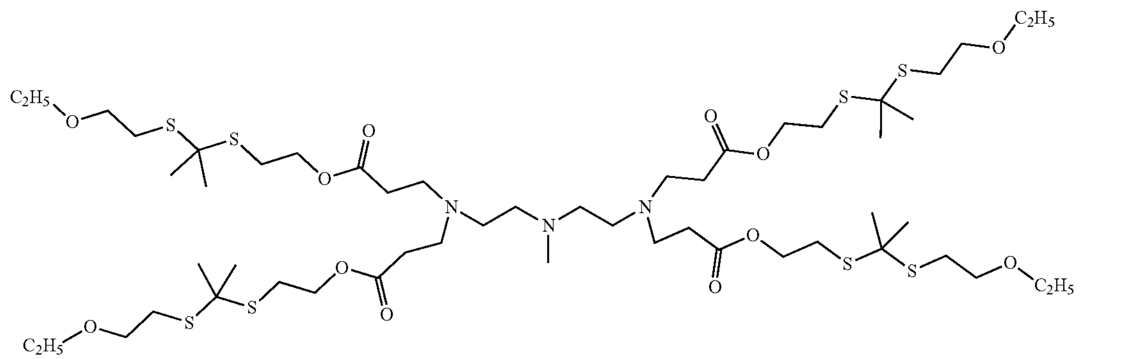

Example 2: Encapsulation of Firefly Luciferase mRNAs, Preparation of Lipid Nanoparticles and the Delivery Experiment In order to achieve spleen-targeted mRNA delivery at animal level, the inventors prepared mRNA/lipid nanoparticles using the method as follows: formulating each of the cationizable lipid compounds (YX-30, YX-32 or YX-34) prepared in Example 1, cholesterol, DOPE and DMG-PEG2000 into a 10 mg/mL ethanol solution. Taking YX-32 as an example, when preparing an mRNA/LNP complex in a single time, the solution of lipid compound YX-30/YX-32/YX-34 (1.1 mg) was measured out and mixed with cholesterol, DOPE and DMG-PEG2000 in a molar ratio of 50:38.5:10:1.5, and the total volume of each solution was solution was 1350 μL. The cationizable lipid compound solution and the mRNA solution were mixed by introducing into a microfluidic machine (speed: 0.2 mL/min of ethanol solution, and 0.6 mL/min of sodium acetate buffer solution) to prepare lipid nanoparticles encapsulating mRNAs, which were dialyzed against PBS buffer for 3 hours, and the obtained samples were directly used for animal experiments. The ratio of the cationizable lipid compound YX-30/YX-32/YX-34 to mRNAs was calculated according to the molar ratio (N/P) of the nitrogen atoms in YX-30/YX-32/YX-34 to the phosphorus atoms in the phosphate skeleton of the mRNAs. In this example, N/P was 7.5.

For lipid nanoparticles encapsulating mRNAs, the concentration of RNAs therein can be detected using QUANT-IT™ RNA assay (Invitrogen Corporation, Carlsbad, CA), so as to evaluate for the RNA encapsulation efficiency of the nanoparticle composition. Samples were diluted in TE buffer (Solarbio, T1120, pH 8.0) to a concentration of about 5 g/mL. 50 μL of the diluted sample was transferred to a polystyrene 96-well plate and 50 μL of TE buffer or 50 μL of 2% Triton X-100 solution (Solarbio, T8200) was added to the wells. The plate was incubated at a temperature of 37° C. for 10 minutes. Reagents were diluted 1:200 in TE buffer and 100 μL of this solution was added to each well. The fluorescence intensity can be measured using a fluorescence plate reader (BIOTEK/Synergy H1) at an excitation wavelength of 480 nm and an emission wavelength of 520 nm, and the percentage of free RNAs was determined by dividing the fluorescence intensity of the intact sample (without addition of Triton X-100) by the fluorescence value of the lysed sample (caused by addition of Triton X-100).

The determination results of encapsulation efficiencies of the three LNPs for RNAs were as follows:

LNPs comprising YX-30: 81.9%;

LNPs comprising YX-32: 52.1%

LNPs comprising YX-34: 53.9%.

In addition, the average particle size, particle dispersion index (PDI) and zeta potential of LNPs were tested by conventional methods in the art.

The test results of LNPs comprising YX-30 in this example were as follows: an average particle size of 188 nm, PDI of 0.01, and a zeta potential of −4.0 mV.

The test results of LNPs comprising YX-32 in this example were as follows: an average particle size of 195 nm, PDI of 0.03, and a zeta potential of −6.0 mV.

The test results of LNPs comprising YX-34 in this example were as follows: an average particle size of 265 nm, PDI of 0.08, and a zeta potential of −3.1 mV.

YX-30 LNPs, YX-32LNPs and YX-34 LNPs encapsulating 150 μg/kg Fluc mRNAs were injected into 6-8 week-old female Balb/c mice by administration via tail vein; after 6 hours, 200 μL of D-Lucifin (with a mass fraction of 30%) was injected by intraperitoneal administration, and the luciferase expression and chemiluminescence intensity in the whole body were detected by PerkinElmer IVIS Lumina III small animal in vivo optical imaging system.

In vivo imaging after delivery of Fluc mRNAs by LNPs comprising lipid compounds YX-30, YX-32 and YX-34 is shown in FIG. 1. FIG. 1 shows that the Luciferase mRNAs delivered by the three LNPs are mainly expressed at the spleen site. Among them, the targeting of the LNPs comprising YX-32 is the best, and the delivery efficiency of the LNPs comprising YX-30 is the highest, but with the slightly worse targeting than that of the LNPs comprising YX-32.

Example 3: Spleen-Targeted Delivery of mRNAs by Lipid Nanoparticles of the Present Invention In order to verify the spleen-targeted delivery effect of the above Fluc mRNA/LNP preparations, YX-32 LNPs encapsulating Fluc mRNAs were injected into 6-8 week-old female Balb/c mice by administration via tail vein (the administered dose of mRNAs was 500 μg/kg; the samples were prepared according to the method described in Example 2); after 6 hours, 200 μL of D-Lucifin (with a mass fraction of 30%) was injected by intraperitoneal administration, and the luciferase expression and chemiluminescence intensity in the whole body were detected by PerkinElmer IVIS Lumina III in vivo optical imaging system for testing in mice. The mice were then sacrificed and dissected to collect tissues, and the treated heart, liver, spleen, lung, and kidney tissues were tested for luciferase expression and chemiluminescence intensity using the PerkinElmer IVIS Lumina III.

Figure 2A:
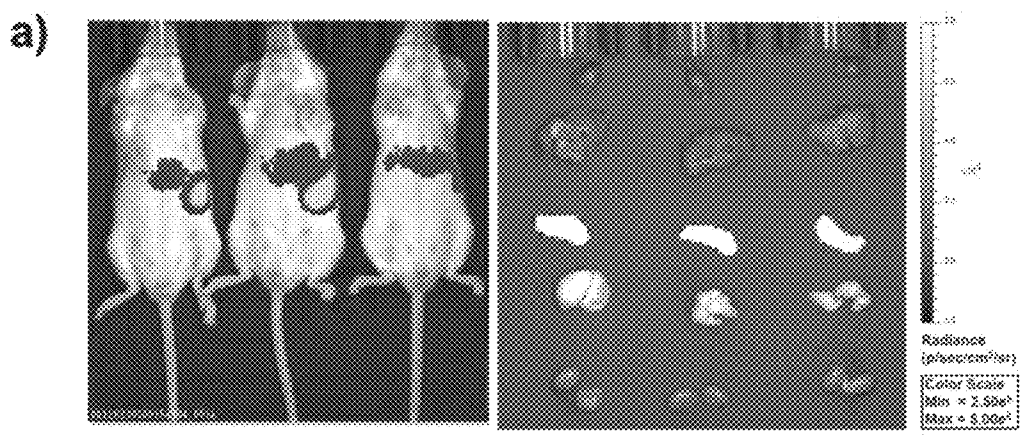
FIG. 2A-B shows in vivo and dissected tissue bioluminescence imaging images after delivery of Firefly luciferase (Fluc) mRNAs by LNPs prepared from lipid compound YX-32 (a), and the ratio of mRNA expression in the spleen/whole body (b).
Figure 2B:
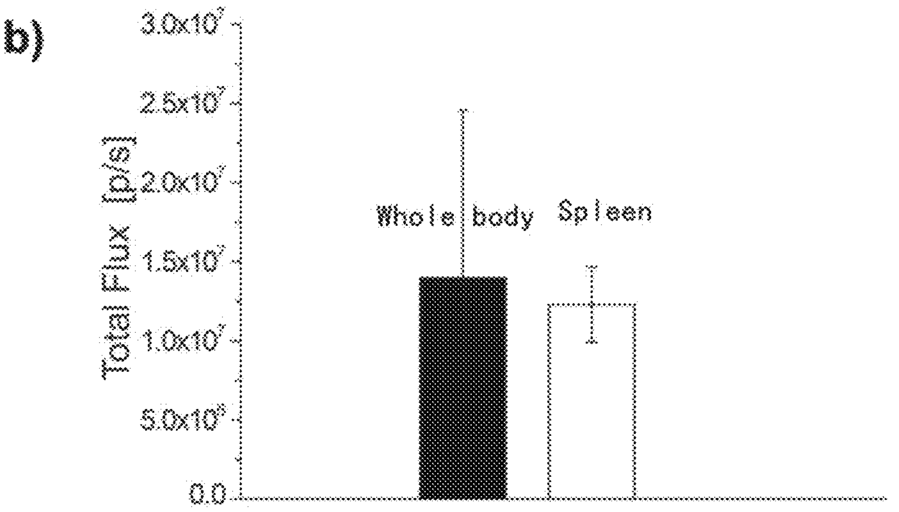

The results are shown in FIG. 2. The left panel of FIG. 2(*a*) shows the in vivo (i.e. the whole body) imaging image, and the right panel of FIG. 2(*a*) shows the tissue imaging image of each organ (including the heart, liver, spleen, lung and kidney). FIG. 2(*b*) shows the luminescence intensity of mRNAs in the whole body and spleen, wherein the ratio of the mRNA expression in the spleen to the mRNA expression in the whole body is as high as 90%, which fully demonstrates the targeted delivery of the LNPs of the present invention to the spleen.

Example 4: The Effect of YX-32 LNP Preparations Comprising Different Ratios of Components on Targeted mRNA Delivery In order to further study the effect of YX-32 LNP preparations comprising different ratios of components on spleen-targeted mRNA delivery, the inventors prepared YX-32/Fluc mRNA preparations comprising different four ratios of components, and studied the expression of luciferase mRNAs at the spleen site when luciferase mRNAs were delivered by these preparations. In view of this, the YX-32 solution (1.1 mg) was measured out and mixed with cholesterol, DOPE and DMG-PEG2000 in different molar ratios (as shown in Table 1), and the total volume of the solution was allowed to reach 450 μL by supplementing ethanol. The method for preparing YX-32 lipid nanoparticles encapsulating Fluc mRNAs was carried out according to the method described in Example 2. The ratio of lipid compound YX-32 to mRNAs was calculated according to the molar ratio (N/P) of the nitrogen atoms in YX-32 to the phosphorus atoms in the phosphate skeleton of the mRNAs, wherein the YX-32-01 preparation was the LNP preparation prepared in Example 2.

TABLE 1

YX-32 LNP preparations useful for spleen-targeted mRNA delivery

| Sample no. | N/P ratio | Lipid | Cholesterol | DOPE | DMG-PEG2000 |
|---|---|---|---|---|---|
| YX-32-01 | 7.5 | 50 | 38.5 | 10 | 1.5 |
| YX-32-02 | 6 | 25 | 48.5 | 25 | 1.5 |
| YX-32-03 | 7.5 | 25 | 48.5 | 25 | 1.5 |
| YX-32-04 | 6 | 15 | 74.5 | 10 | 0.5 |
| YX-32-05 | 7.5 | 15 | 74.5 | 10 | 0.5 |
| YX-32-06 | 7.5 | 20 | 60 | 19.5 | 0.5 |
| YX-32-07 | 7.5 | 25 | 65 | 9.5 | 0.5 |
| YX-32-08 | 7.5 | 30 | 60 | 9.5 | 0.5 |
| YX-32-09 | 9 | 25 | 65 | 9.5 | 0.5 |

Figure 3:
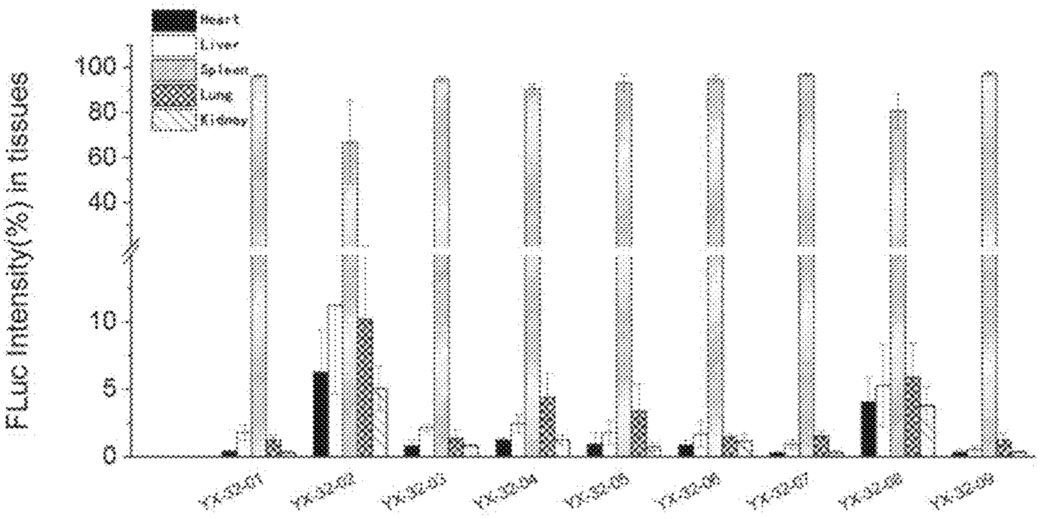
FIG. 3 shows luciferase intensity analysis in different tissues of mice after delivery of Fluc mRNAs by different YX-32 LNP preparations.

In the same manner as in Example 3, 6-8 week-old female Balb/c mice were injected with each YX-32 LNP preparation encapsulating 500 μg/kg of Fluc mRNAs by administration via tail vein; after 6 hours, the mice were sacrificed and dissected to collect tissues (the heart, liver, spleen, lung, and kidney) which were placed in PBS to clean the surface and weighed. 100 mg of tissues were taken and added to 500 μL of formulated tissue lysis solution (IP cell lysis solution comprising 1 mM PMSF), and then the mixture was transferred to crushed ice for tissue homogenization (35000 revolutions, 10 seconds each time, repeated three times with an interval of 10 seconds between adjacent repetitions). The lysate was centrifuged at 4° C. for 15 minutes, and the supernatant was taken for later use and the protein concentration was quantified by the BCA method. 500 g of lysates from different tissues were taken, the luciferase activity in different tissues lysates was detected using the luciferase activity system (Promega, E1501) kit, and the proportions of luciferase enzyme activity in 5 different tissue lysates were calculated. FIG. 3 shows the expression level of luciferase in the spleen and the proportions of enzyme activity in the five types of tissues of heart, liver, spleen, lung and kidney as high as 65% or more, and even as high as 90% or more, after delivery of mRNAs by LNP preparations of different components.

Figure 4:
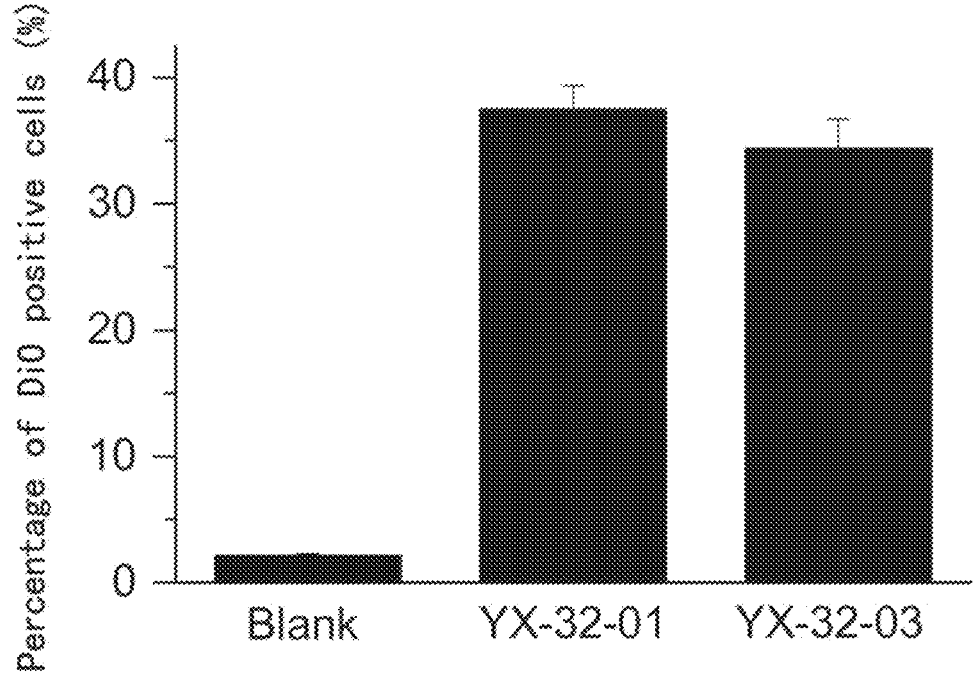
FIG. 4 shows analysis of splenic cell uptake of YX-32/Fluc mRNA nanoparticles.

Example 5: Preparation of YX-32/mRNA Lipid Nanoparticles Labeled with DiO Fluorescence and Cell Uptake Experiment In order to further verify that the expression of luciferase after the administration of YX-32/mRNA lipid nanoparticles is related to the uptake of YX-32/mRNAs by spleen cells, the inventors carried out the preparation of fluorescently labeled mRNA/lipid nanoparticles and studied the cell uptake efficiency. The specific method was as follows: 13 μL of DiO solution in ethanol (10 mg/mL) was added to the YX-32/Fluc mRNA lipid nanoparticles prepared in Example 1, and mixed evenly in the dark. The mixture was dialyzed using PBS as the buffer for 3 hours in the dark, and the obtained sample was directly used for the animal experiment. In order to further study the uptake efficiency of YX-32/Fluc mRNAs by spleen cells, LNPs encapsulating 500 μg/kg of DiO-labeled YX-32/Fluc mRNAs were injected into 6-8 week-old female Balb/c mice by administration via tail vein; after 6 hours, the mice were sacrificed and dissected to collect the spleen tissue, and the surface of the tissue was washed in PBS. The spleen tissue was added to 250 μL of digestion solution (DMEM cell culture medium containing 45 U/μL of collagenase 1+25 U/μL of DNAse I+30 U/μL of hyaluronidase 1) and minced with a sterile blade. The minced spleen and digestion solution were transferred to a 15 mL tube, 5-10 mL of digestion solution was added, and the mixture was incubated in a constant temperature incubator at 37° C. and shaken for 1 hour. After removing, the mixture was filtered through a 70 m cell strainer, the tube and strainer were rinsed with PBS (containing 2% FBS) to make the total amount of liquid up to 10 mL. The above cell suspension was centrifuged under a condition at 4° C. for 5 minutes (speed: 300 G), and then the supernatant was discarded. The cell pellet was then resuspended with 2 mL of red blood cell lysis solution, and lysed in an ice bath for 5 minutes, during which the red blood cells were fully lysed by shaking several times. The red blood cell lysis was stopped by addition of 4 mL of PBS (containing 2% FBS), the above cell suspension was centrifuged under a condition at 4° C. for 5 minutes (speed: 300 G), and then the supernatant was discarded. The cell pellet was resuspended with 1 mL of PBS (containing 2% FBS). After resuspension, the suspension was filtered with a 70 m cell strainer, the filtrate was pipetted and blown to mix evenly, and the DiO positive ratio was detected and analyzed by a flow cytometer, that is, the cell uptake efficiency of YX-32/Fluc mRNA LNPs. The results showed that the efficiency of uptake of YX-32/mRNA lipid nanoparticles by spleen cells was about 35% or more (FIG. 4).

The above description is only preferred embodiments of the present invention; however, the scope of protection of the present invention is not limited thereto. Any changes or substitutions readily conceivable to those familiar with the technical field within the technical scope disclosed by the present invention should be covered by the scope of protection of the present invention. Therefore, the scope of protection of the present invention should be based on the scope of protection of the claims.

The invention claimed is:

1. A lipid compound of formula (I),

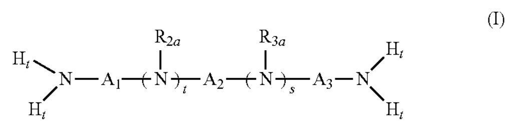

(I)

wherein $R_{2a}$ and $R_{3a}$ are each independently selected from the group consisting of hydrogen, a monovalent aliphatic group, a monovalent heteroaliphatic group, a monovalent aromatic group, a monovalent heteroaromatic group, and Ht;

t and s are each independently 0 or 1, and when t or s is zero, it means that the part is directly a single bond, provided that t and s are not both 0;

$A_1$, $A_2$, and $A_3$ are each independently selected from the group consisting of a single bond, a divalent aliphatic group, a divalent heteroaliphatic group, a divalent aromatic group, and a divalent heteroaromatic group;

each Ht is independently at each occurrence $-R_1-X-R_2-Y-R_3-Z-R_4$, wherein each $R_1$ is independently at each occurrence selected from the group consisting of a divalent aliphatic group, a divalent heteroaliphatic group, a divalent aromatic group, and a divalent heteroaromatic group;

each X is independently at each occurrence

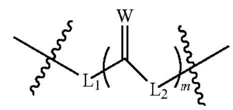, wherein m is 1-6;

W is selected from the group consisting of O, S, and $NR_c$;

$L_1$ is directly connected to $R_1$ or $R_2$ and is independently selected from the group consisting of a single bond, O, S, and $NR_d$;

$L_2$ independently is selected from the group consisting of a bond, O, S, and $NR_e$;

wherein $R_c$, $R_d$, and $R_e$, are each independently selected from the group consisting of hydrogen, hydroxy, an oxyaliphatic group, a monovalent aliphatic group, a monovalent heteroaliphatic group, a monovalent aromatic group, and a monovalent heteroaromatic group;

Y and Z are each independently at each occurrence selected from the group consisting of S and O;

each $R_2$ is independently at each occurrence selected from the group consisting of a single bond, a divalent aliphatic group, a divalent heteroaliphatic group, a divalent aromatic group, and a divalent heteroaromatic group;

$R_3$ is independently at each occurrence

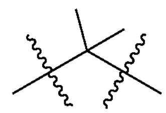;

each $R_4$ is independently at each occurrence a hydrophobic group selected from the group consisting of $-(CH_2CH_2O)_y-C_{1-2}$ alkyl, $-(CH_2CH_2O)_y-C_2$ alkenyl and $-(CH_2CH_2O)_y-C_2$ alkynyl, wherein y is 0 or 1 or 2.

2. The lipid compound of claim 1, wherein t is 0 and s is 1; or t is 1 and s is 0.

3. The lipid compound of claim 1, wherein $R_1$ is selected from the group consisting of a $C_{1-6}$ divalent aliphatic group and a $C_{1-6}$ divalent heteroaliphatic group.

4. The lipid compound of claim 1, wherein $L_1$ is connected to $R_1$ and is independently selected from the group consisting of a single bond, O, S, and NH.

5. The lipid compound of claim 1, wherein X is selected from the group consisting of

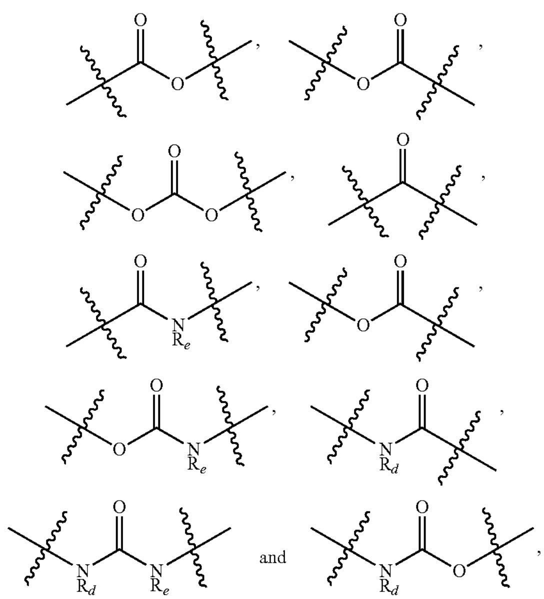

wherein $R_d$ and $R_e$ are as defined for formula (I).

6. The lipid compound of claim 5, wherein $R^d$ and $R^e$ are each independently selected from the group consisting of H and a $C_{1-4}$ monovalent aliphatic group.

7. The lipid compound of claim 1, wherein Y and Z are both S; or Y is S and Z is O; or Y is O and Z is S; or Y and Z are both O.

8. The lipid compound of claim 1, wherein each $R_2$ is independently at each occurrence selected from the group consisting of a single bond and a $C_{1-6}$ divalent aliphatic group.

9. The lipid compound of claim 8, wherein each $R_2$ is independently at each occurrence a $C_{1-4}$ divalent aliphatic group.

10. The lipid compound of claim 1, wherein each $R_4$ is independently at each occurrence selected from the group consisting of ethyl ($C_2H_5$), methyl ($CH_3$), ethenyl, ethynyl, $-(CH_2CH_2O)-CH_3$, $-(CH_2CH_2O)-C_2H_5$, $-(CH_2CH_2O)-CH-CH_2$, $-(CH_2CH_2O)-C{=}CH$, $-(CH_2CH_2O)_2-CH_3$, $-(CH_2CH_2O)_2-C_2H_5$, $-(CH_2CH_2O)_2-CH{\equiv}CH_2$ and $-(CH_2CH_2O)_2-C{\equiv}CH$.

11. The lipid compound of claim 1, wherein each Ht is independently at each occurrence

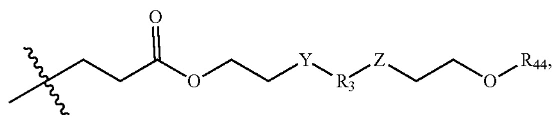

wherein Y and Z are both S; or Y is S and Z is O; or Y is O and Z is S; or Y and Z are both O; each $R_3$ is independently at each occurrence a

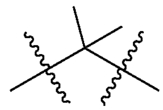

and $R_{44}$ is selected from the group consisting of ethyl ($C_2H_5$), methyl ($CH_3$), ethenyl and ethynyl.

12. The lipid compound of claim 1, wherein t is 1, s is 0, $A_2$ is a single bond, and $A_1$ and $A_3$ are each independently selected from the group consisting of a divalent aliphatic group and a divalent heteroaliphatic group;

t is 1, s is 0, $A_2$ is a single bond, and $A_1$ and $A_3$ are each independently a $C_{1-6}$ divalent aliphatic group;

t is 1, s is 0, $A_2$ is a single bond, $A_1$ and $A_3$ are each independently selected from the group consisting of $-CH_2CH_2-$ and $-CH_2CH_2CH_2-$, and $R_{2a}$ is selected from the group consisting of hydrogen and a monovalent aliphatic group.

13. The lipid compound of claim 1, wherein t is 1, s is 1, and $A_1$, $A_2$ and $A_3$ are each independently selected from the group consisting of a divalent aliphatic group and a divalent heteroaliphatic group;

t is 1, s is 1, and $A_1$, $A_2$ and $A_3$ are each independently a $C_1$-$C_6$ divalent aliphatic group;

t is 1, s is 1, and $A_1$, $A_2$ and $A_3$ are each independently selected from the group consisting of $-CH_2CH_2-$ and $-CH_2CH_2CH_2-$, and $R_{2a}$ and $R_{3a}$ are each independently selected from the group consisting of hydrogen and a monovalent aliphatic group.

14. The lipid compound of claim 1, wherein

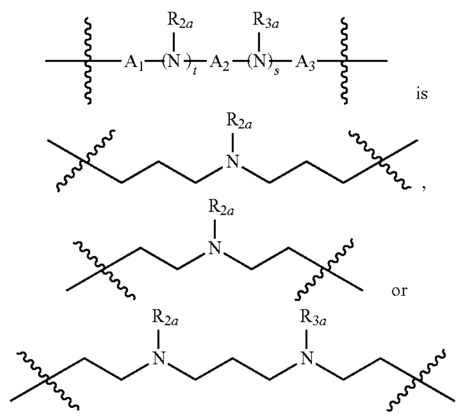

wherein $R_{2a}$ and $R_{3a}$ are each independently selected from the group consisting of hydrogen and a monovalent aliphatic group.

15. A lipid compound selected from the group consisting of
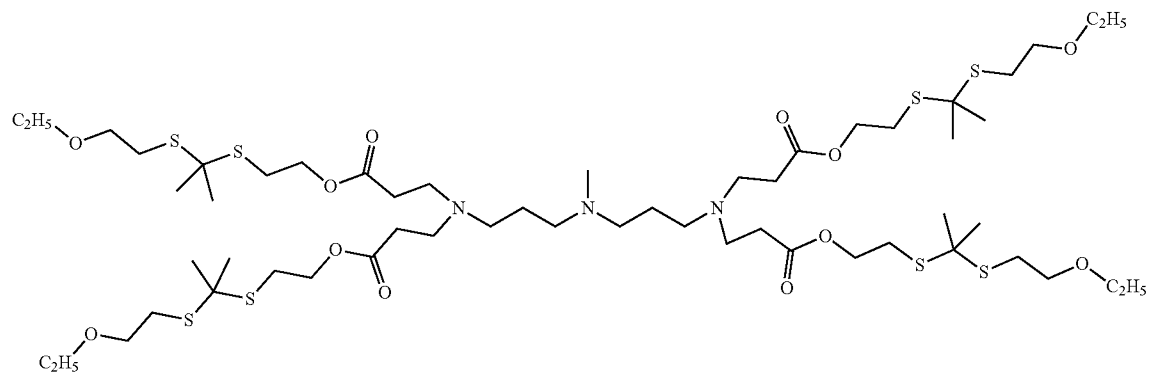
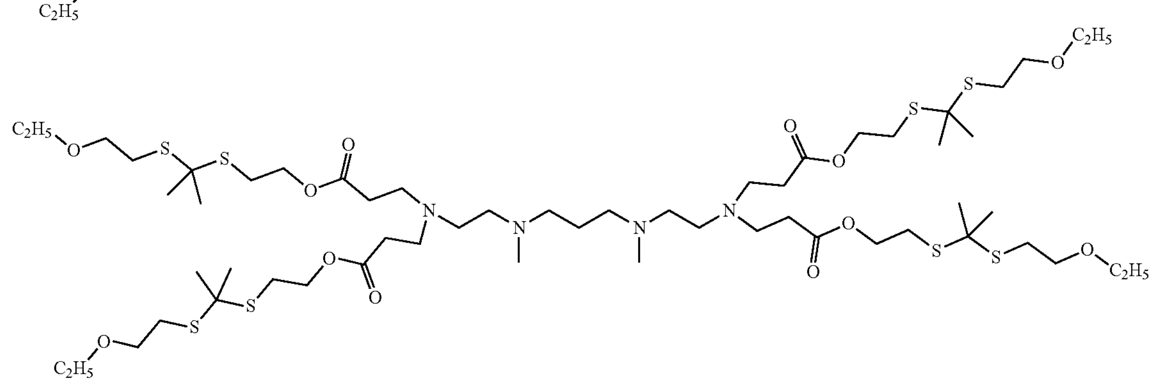
and
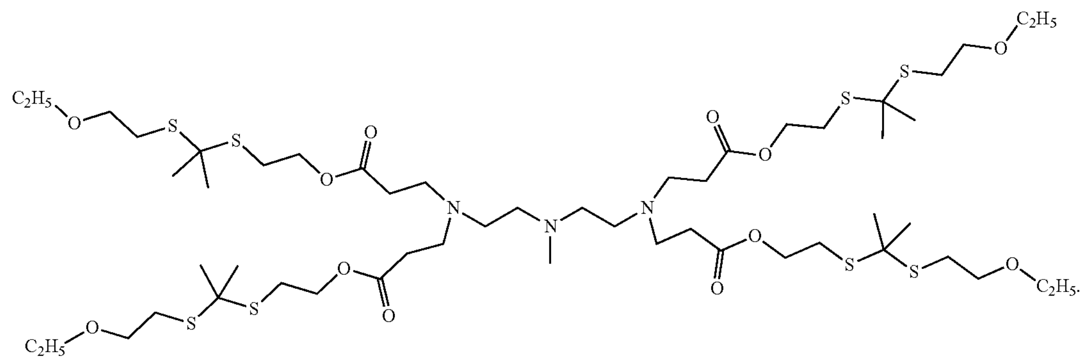
* * * * *